(12) United States Patent
Okamura

(10) Patent No.: US 9,320,873 B2
(45) Date of Patent: Apr. 26, 2016

(54) INTRODUCER SHEATH AND INTRODUCER ASSEMBLY

(75) Inventor: Ryo Okamura, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 605 days.

(21) Appl. No.: 13/495,496

(22) Filed: Jun. 13, 2012

(65) Prior Publication Data
US 2012/0323182 A1 Dec. 20, 2012

(30) Foreign Application Priority Data

Jun. 15, 2011 (JP) .................................. 2011-133601
Apr. 11, 2012 (WO) .................. PCT/JP2012/059908

(51) Int. Cl.
*A61M 25/00* (2006.01)
*A61M 25/06* (2006.01)
*A61M 25/01* (2006.01)

(52) U.S. Cl.
CPC ....... *A61M 25/0662* (2013.01); *A61M 25/0045* (2013.01); *A61M 25/01* (2013.01); *A61M 2025/0046* (2013.01); *A61M 2025/0047* (2013.01); *A61M 2025/0687* (2013.01); *A61M 2205/0222* (2013.01)

(58) Field of Classification Search
CPC ............ A61M 25/01; A61M 25/0102; A61M 2005/1585; A61M 2025/0046; A61M 2420/08; A61M 25/0045; A61M 25/0047; A61M 25/0048; A61M 2025/0062; A61M 2205/0222; A61M 2025/0687; A61L 29/00; A61L 29/08; A61L 29/12; A61L 29/14; A61L 29/145; A61L 2400/10

USPC ......... 604/164.01, 164.1, 171, 172, 265, 230, 604/264
See application file for complete search history.

(56) References Cited

U.S. PATENT DOCUMENTS

| 5,011,478 A | 4/1991 | Cope |
| 5,304,142 A | 4/1994 | Liebl et al. |
| 5,902,631 A * | 5/1999 | Wang et al. .................... 427/2.1 |
| 6,458,867 B1 | 10/2002 | Wang et al. |

(Continued)

FOREIGN PATENT DOCUMENTS

| CN | 1655840 A | 8/2005 |
| CN | 1868552 A | 11/2006 |

(Continued)

OTHER PUBLICATIONS

Extended European Search Report dated Oct. 30, 2014, issued by the European Patent Office in the corresponding European Application No. 12801433.9. (8 pages).

(Continued)

*Primary Examiner* — Bhisma Mehta
*Assistant Examiner* — Laura Schell
(74) *Attorney, Agent, or Firm* — Buchanan Ingersoll & Rooney PC

(57) ABSTRACT

An introducer sheath, which is formed from a tubular member provided with a hollow portion through which an elongated body is freely insertable, and which includes a distal portion and a main body portion, wherein the inner diameter of the distal portion is formed to become gradually smaller toward the distal side, and on the inner surface of the distal portion, there is provided a hydrophobic coating having a friction coefficient lower than the friction coefficient of the tubular member.

15 Claims, 7 Drawing Sheets

(56) References Cited

U.S. PATENT DOCUMENTS

| | | | |
|---|---|---|---|
| 6,999,809 B2* | 2/2006 | Currier et al. | 600/342 |
| 2002/0026145 A1* | 2/2002 | Bagaoisan et al. | 604/96.01 |
| 2006/0259011 A1 | 11/2006 | Kubo et al. | |
| 2007/0129690 A1* | 6/2007 | Rosenblatt et al. | 604/265 |
| 2008/0097397 A1 | 4/2008 | Vrba | |

FOREIGN PATENT DOCUMENTS

| | | |
|---|---|---|
| EP | 0450221 A1 | 10/1991 |
| EP | 0901392 B1 | 3/2004 |
| EP | 1878453 A1 | 1/2008 |
| JP | H02-246984 A | 10/1990 |
| JP | H03-289967 A | 12/1991 |
| JP | 2001-508670 A | 7/2001 |
| JP | 2002-503989 A | 2/2002 |
| JP | 2002-291902 A | 10/2002 |
| JP | 2003-510134 A | 3/2003 |
| JP | 2003-325671 A | 11/2003 |
| JP | 2009-539487 A | 11/2009 |
| WO | 98/55172 A2 | 12/1998 |
| WO | 99/44665 A2 | 9/1999 |
| WO | 0123015 A1 | 4/2001 |
| WO | 03090814 A2 | 11/2003 |
| WO | 2006/1118103 A1 | 11/2006 |
| WO | 2007/103772 A2 | 9/2007 |
| WO | 2007122908 A1 | 11/2007 |
| WO | 2007/143280 A1 | 12/2007 |
| WO | 2012172861 A1 | 12/2012 |

OTHER PUBLICATIONS

Office Action issued on May 6, 2015, by the State Intellectual Property Office of the People's Republic of China in corresponding Chinese Patent Application No. 201580028891.0 (8 pages).

Examination Report issued on Apr. 24, 2015, by the Intellectual Property Office of Singapore in corresponding application No. 2013080825. (10 pages).

International Search Report issued on Jul. 10, 2012, by the Japanese Patent Office in its capacity on the International Searching Authority in counterpart International Application No. PCT/JP2012/059908.

Australian Patent Examination Report corresponding to Australian Patent Application No. 2012270850, dated Oct. 27, 2015; 3 pages.

Second Office Action issued on Jan. 14, 2016, by the State Intellectual Property Office of the People's Republic of China in the corresponding Chinese Patent Application No. 2012800288981.0 and English translation (10 pages).

Notification of Reasons for Refusal dated Feb. 23, 2016 issued by the Japanese Patent Office in the corresponding Japanese Patent Application No. 2013-520453 and English translation (9 pages).

* cited by examiner

INTRODUCER SHEATH AND INTRODUCER ASSEMBLY

CROSS REFERENCES TO RELATED APPLICATIONS

This application contains subject matter disclosed in Japanese Patent Application JP2011-133601 filed in the Japanese Patent Office on Jun. 15, 2011 and International Application No. PCT/JP2012/059908 filed on Apr. 11, 2012, the entire content of both of which is incorporated herein by reference.

FIELD OF THE INVENTION

The present invention generally relates to an introducer sheath and an introducer assembly.

BACKGROUND DISCUSSION

In recent years, various forms of medical treatment and checkups have been performed using an elongated hollow and tubular medical instrument referred to as a catheter. Examples of such medical treatment methods include administering medicine directly into a target lesion by utilizing the elongated property of the catheter, pushing, widening and opening a stenosis region inside a lumen in a living body (e.g., blood vessel) using a catheter equipped with a balloon, which spreads by pressurization, at the distal end of the catheter, a shaving off and opening a target lesion using a catheter equipped with a cutter at the distal portion of the catheter, applying a filler and closing an aneurysm, a bleeding place or a feeding vessel using a catheter. Also, there exists a medical treatment method in which in order to maintain a stenosis region inside a lumen in a living body in an opened state, a tube-shaped stent constituted to be in the shape of net for the side surface thereof is embedded and indwelled inside a lumen in a living body by using a catheter, or the like. Further, there exists a method of sucking a liquid which has become excessive for the internal body, or the like.

In case of carrying out a medical treatment and checkup or the like using a catheter, generally, an introducer sheath is introduced into a sticking region formed in an arm or a leg by using a catheter introducer and a catheter or the like is percutaneously inserted into a diseased region such as a blood vessel or the like through a lumen of the introducer sheath.

The introducer sheath is formed from a sheath tube which is a tubular member provided with a hollow portion through which an elongated body such as a catheter is freely insertable (see Japanese Unexamined PCT Patent Publication No. 2003-510134 and Japanese Unexamined Patent Publication No. 2002-291902). In Japanese Unexamined PCT Patent Publication No. 2003-510134, there is described a configuration of providing a hydrophilic coating on the inner surface of an introducer sheath in order to reduce sliding resistance when inserting an elongated body such as a catheter through the introducer sheath. Also, Japanese Unexamined Patent Publication No. 2002-291902 describes providing a hydrophilic coating on the outer surface of an introducer sheath in order to secure the lubricity of the outer surface of the introducer sheath. Japanese Unexamined Patent Publication No. 2002-291902 also describes an introducer sheath in which the inner diameter at the distal portion thereof is formed to become gradually smaller toward the distal side (see FIG. 4 of Japanese Unexamined Patent Publication No. 2002-291902).

When the inner diameter of the distal portion is formed gradually in smaller size toward the distal side as described in Japanese Unexamined Patent Publication No. 2002-291902 sliding resistance between the inner surface of the distal portion and elongated body such as a catheter becomes large and there occurs a phenomenon that slidability of the catheter or the like is lowered. In order to improve such a situation, it is conceivable, as described in Japanese Unexamined PCT Patent Publication No. 2003-510134, that there is provided a hydrophilic coating on the inner surface of the introducer sheath. However, the heat that is produced at the time of carrying out a shape-application process of the distal portion using a die assembly acts excessively, and there occurs a phenomenon that the hydrophilic coating will peel, will decompose, will degrade or the like. Consequently, the sliding resistance between the inner surface of the distal portion and the elongated body such as a catheter is not lowered substantially and so a difficulty arises in that it is not possible to achieve improvement in the slidability of the catheter or the like.

Also, when pulling out the introducer sheath after being inserted inside the blood vessel in a case in which there is provided a hydrophilic coating on the outer surface of the sheath as described in Japanese Unexamined Patent Publication No. 2002-291902, the hydrophilic coating becomes wet by the blood, lubricity occurs and a situation results in which the friction resistance is small. Consequently, it is possible to pull out the introducer sheath rather smoothly. However, at the beginning of the use of the introducer sheath, the hydrophilic coating is under a dry condition, so that the sliding property is bad and the friction resistance thereof is large. Consequently, when inserting it from the skin toward the inside of the blood vessel, the insertion resistance of the introducer sheath is undesirably large.

SUMMARY

An introducer sheath is disclosed in which the slidability of an elongated body such as a catheter or the like is achieved even in case of the inner diameter of the distal portion being tapered so that the inner diameter becomes gradually smaller toward the distal end.

The disclosure here also describes an introducer sheath in which a reduction in insertion resistance is achieved even under a dry condition at the beginning of the use thereof. The introducer assembly is also configured to make it possible to insert the introducer sheath rather smoothly by suppressing a turn-up of the distal portion.

According to one aspect of the disclosure here, an introducer sheath is formed from a tubular member provided with a hollow portion through which an elongated body is freely insertable, and which includes a distal portion and a main body portion, and wherein the inner diameter of the distal portion is formed to become gradually smaller toward the distal side, and on the inner surface of the distal portion, there is provided a hydrophobic coating having a friction coefficient lower than the friction coefficient of the tubular member.

Another aspect of the disclosure involves an introducer sheath, which is formed from a tubular member provided with a hollow portion through which an elongated body is freely insertable, and which includes a distal portion and a main body portion, wherein there is provided a hydrophilic lubricating coating on the outer surface of the main body portion, on the outer surface of the distal portion, there is provided a hydrophobic coating having a friction coefficient lower than the friction coefficient of the hydrophilic lubricating coating during the dry period thereof.

Still another aspect of the disclosure involves an introducer assembly formed by inserting a dilator as the elongated body through the introducer sheath described above and by projecting a distal end of the dilator from the distal portion of the introducer sheath. Then, at least a portion of the inner surface of the distal portion of the introducer sheath and a portion of the outer surface of the dilator are attached through the hydrophobic coating.

The inner diameter of the distal portion gradually becomes smaller toward the distal side, and the inner surface of the distal portion is provided with a hydrophobic coating having a friction coefficient lower than the friction coefficient of the tubular member. Consequently, even in case of forming the inner diameter of the distal portion gradually smaller toward the distal side, it is possible to provide an introducer sheath in which improvement in the slidability of an elongated body such as a catheter or the like is achieved.

It is preferable for the outer surface of the distal portion to be further provided with a hydrophobic coating. In this case, it is possible to achieve reduction in insertion resistance even under a dry condition at the beginning of the use thereof.

A hydrophilic lubricating coating is preferably also provided on the outer surface of the main body portion, and a hydrophilic coating can be provided on the outer surface of the distal portion, with the hydrophobic coating having a friction coefficient lower than the friction coefficient of the hydrophilic lubricating coating during the dry period (i.e., before liquid is applied to the hydrophilic lubricating coating). Consequently, even under a dry condition at the beginning of use, it is possible to provide an introducer sheath in which reduction in insertion resistance is achieved.

It is preferable for the hydrophobic coating to cover the upper portion of the hydrophilic lubricating coating at the boundary portion between the distal portion and the main body portion. In this case, when inserting the introducer sheath from the skin into the inside of the blood vessel, it never happens that the sheath gets stuck on the end surface of the hydrophilic lubricating coating at the boundary portion. Consequently, it is possible to insert the introducer sheath smoothly and it is possible to suppress peeling of the hydrophilic lubricating coating.

When absorbing the blood and swelling, it is preferable for the hydrophilic lubricating coating to exhibit a diameter approximately equal to or greater than the outer diameter of the hydrophobic coating. For example, when the hydrophilic lubricating coating swells by absorbing blood, the hydrophilic lubricating coating has a diameter approximately equal to or greater than the outer diameter of the overlapping portion in which the hydrophobic coating overlaps the hydrophilic lubricating coating. In this case, when pulling out the introducer sheath from the blood vessel, a step does not exist at the overlapping portion in which the hydrophobic coating axially overlaps the hydrophilic lubricating coating. Consequently, the resistance of the surface of the introducer sheath with respect to the blood vessel and the skin does not become surplus and it is possible to pull out the introducer sheath relatively smoothly owing to both the coatings.

At least a portion of the inner surface of the distal portion of the introducer sheath and a portion of the outer surface of the dilator are attached to each other through hydrophobic coating. Attaching the distal portion and the dilator to each other through hydrophobic coating helps suppress turn-up of the distal portion when inserting the introducer sheath and to insert the introducer sheath rather smoothly.

It is preferable for the hydrophobic coating to be formed from a reactive-curing coating material and to be formed by reactively curing the coating material in a state in which the dilator is passed through the introducer sheath. In this case, it is possible to carry out the formation of the hydrophobic coating and the attachment between the inner surface of the distal portion and the outer surface of the dilator through this hydrophobic coating simultaneously, and it is possible to achieve simplification of the manufacturing process.

It is preferable the introducer assembly be configured so that the force by which the introducer sheath and the dilator are attached to each other is smaller than the force which acts on the attachment region when the dilator is pulled out from the introducer sheath. In this case, by employing a configuration in which the attachment region is breakable in conjunction with the operation of pulling out the dilator, it is possible to handle the introducer assembly while maintaining similar feeling as heretofore and it never brings uncomfortable feeling to the user.

It is preferable to attach the introducer sheath and the dilator by reactively curing the coating material depending on heat at the time of gas sterilization. In this case, it is possible to carry out the formation of the hydrophobic coating and the attachment between the introducer sheath and the dilator through this hydrophobic coating in a packed state simultaneously at the time of gas sterilization, and it is possible to achieve simplification of the manufacturing process.

According to another aspect, an introducer sheath comprises: an elongated tubular member configured to be inserted in a living body tissue and including a distal portion and a main body portion, with the distal portion terminating distally at a distal-most end of the distal portion; and the distal-most end of the tubular member and the distal-most end of the distal portion being the same; and the main body portion having a distal-most end connected to and extending proximally from a proximal-most end of the distal portion so that the main body portion is located entirely proximally of the distal portion, the main body portion possessing an outer surface. The elongated tubular member includes a through hole extending throughout a longitudinal extent of the tubular member and opening to the distal-most end of the elongated tubular member, with the through hole being configured to receive an elongated body. The elongated tubular member is comprised of a taper portion in which the inner diameter of the through hole gradually and continuously tapers to the distal-most end of the elongated tubular member so that the inner diameter of the through hole in the taper portion is smaller at the distal-most end of the taper portion than at a proximal-most end of the taper portion. A hydrophilic lubricating coating is on the outer surface of the main body portion, and a hydrophobic coating is on the inner surface of the through hole in the taper portion, the hydrophobic coating extending proximally from the distal-most end of the tubular member toward the main body portion. The hydrophobic coating possesses a friction coefficient lower than the friction coefficient of the hydrophilic lubricating coating before the hydrophilic lubricating coating contacts liquid.

BRIEF DESCRIPTION OF THE DRAWINGS

Other aspects and characteristics of the introducer sheath and the introducer assembly disclosed here will become more apparent from the following detailed description of embodiments disclosed as examples, considered with reference to the accompanying drawing figures which illustrate the embodiments disclosed as examples.

DETAILED DESCRIPTION

Figure 1:
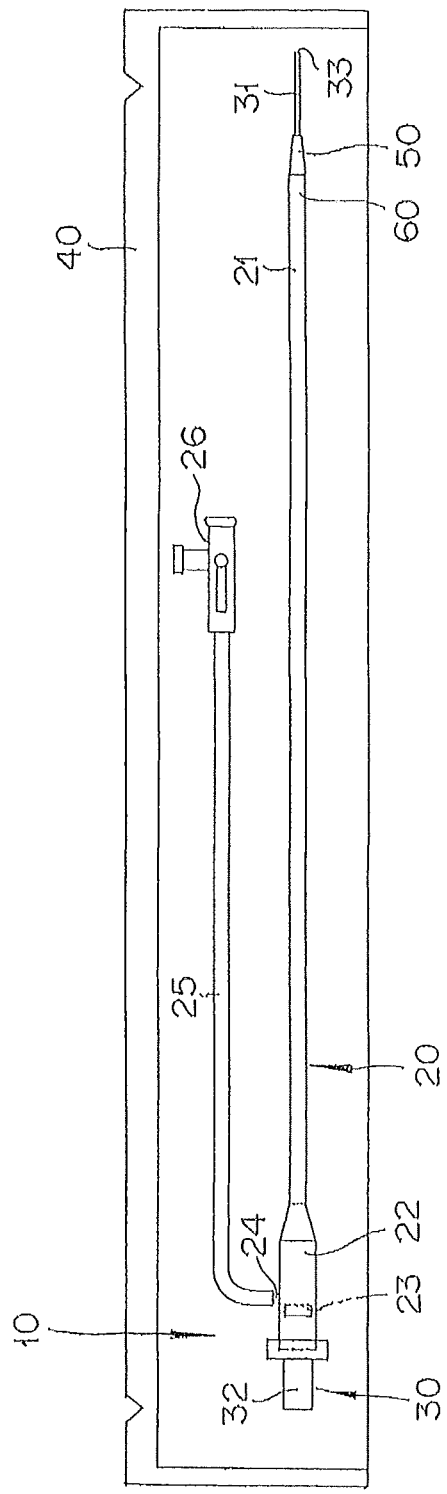
FIG. 1 is a plan view of an introducer assembly disclosed here by way of example packaged inside a packaging film.

Set forth below with reference to the attached drawings is a detailed description of examples of the introducer sheath and introducer assembly disclosed here. The drawings identify common features by common reference numerals, and so a detailed discussion of such features and aspects of the sheath and assembly which are the same as previously described will not be repeated. Also, the size ratio of features shown in the drawings is exaggerated for convenience of explanation and it is different from the actual ratio.

An introducer assembly 10 is a device for securing or providing an access route to the inside of a lumen in a living body (e.g., a blood vessel). In the following explanation, the hand-side operation unit side or end of the device is referred to as the "proximal side" or "proximal end", and the side or end to be inserted into the inside of the lumen in a living body is referred to as the "distal side" or "distal end".

Figure 2:
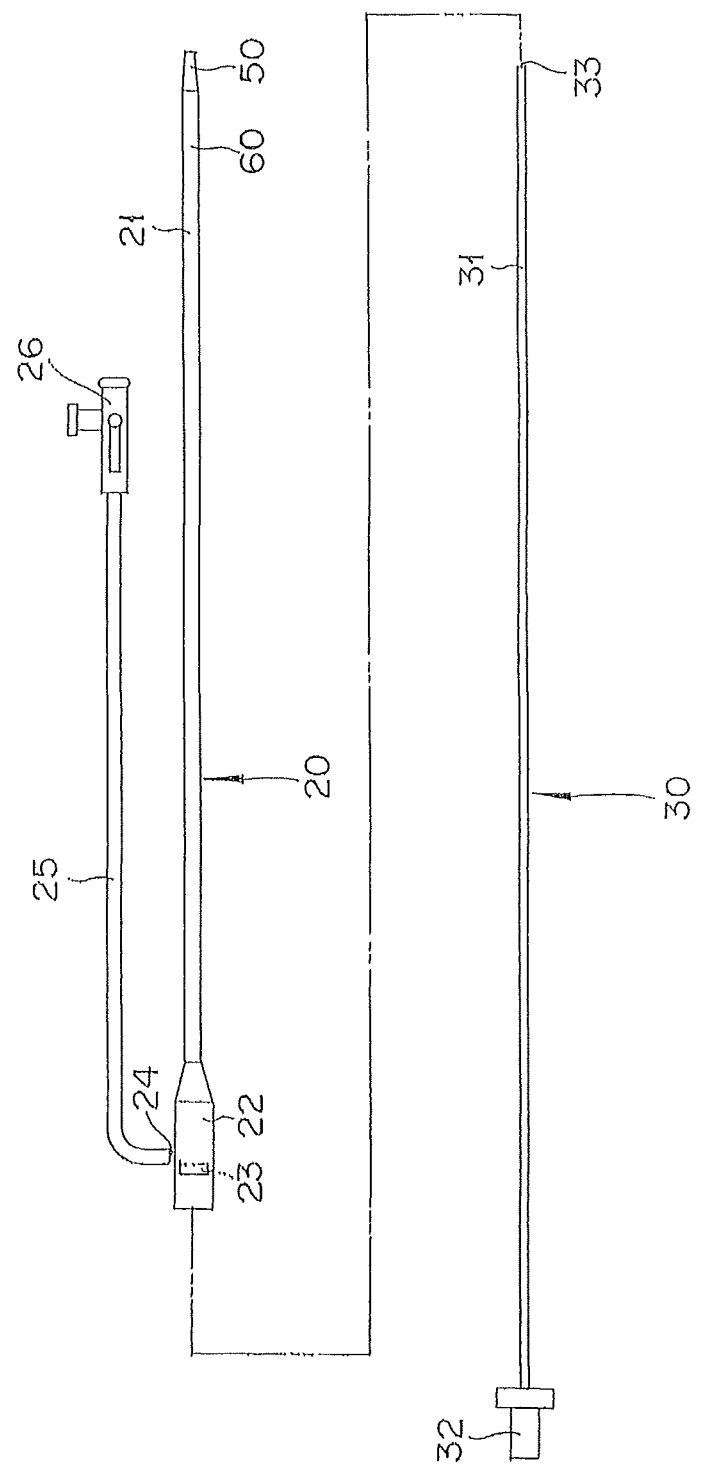
FIG. 2 is an exploded plan view of an introducer sheath and a dilator of an introducer assembly.

FIG. 1 illustrates the introducer assembly 10 packaged inside a packaging film 40, and FIG. 2 illustrates, in an exploded manner, a sheath 20 for introducer and a dilator 30 of the introducer assembly 10.

Generally speaking, and with reference to FIG. 1 and FIG. 2, the introducer assembly 10 includes the introducer sheath 20 and the dilator 30. In this embodiment disclosed as one example of the introducer assembly, the introducer sheath 20 and the dilator 30 are integrated beforehand and packaged inside the packaging film 40. That is, the integrated introducer sheath 20 and dilator 30 are entirely covered by and enclosed within the packaging film in a sterile state. The introducer sheath 20 is provided with a sheath tube 21, a sheath hub 22 attached to the proximal end of the sheath tube 21, and a hemostasis valve 23 attached to the proximal end of the sheath hub 22. The dilator 30 is provided with a dilator tube 31 and a dilator hub 32 attached to the proximal end of the dilator tube 31. The introducer assembly 10 will now be described in more detail.

The introducer sheath 20 is indwelled inside the lumen in a living body and is a sheath for being introduced into the inside of the lumen in a living body, with an elongated body such as a catheter, a guide wire, an embolus object or the like being inserted therethrough in the inside thereof.

The sheath tube 21 is introduced percutaneously into the inside of the lumen in a living body (e.g., blood vessel).

As the constituent material of the sheath tube 21, it is possible to use, for example, a polymer material such as a polyolefin (e.g. polyethylene, polypropylene, polybutene, ethylene-propylene copolymer, ethylene-vinyl acetate copolymer, ionomer, a mixture of two kinds or more of these, or the like), polyolefin elastomer, a cross-linked body of polyolefin, polyvinyl chloride, polyamide, polyamide elastomer, polyester, polyester elastomer, polyurethane, polyurethane elastomer, fluororesin, polycarbonate, polystyrene, polyacetal, polyimide, polyetherimide or the like, a mixture of these, or the like. It is possible to use ethylenetetrafluoroethylene copolymer (ETFE) favorably.

A side port 24 which communicates with the inside of the sheath tube 21 is formed at the sheath hub 22. One end of a tube 25 having flexibility, which is made, for example, of polyvinyl chloride, is connected to the side port 24 in a liquid-tight manner. On the other end of the tube 25, for example, a T-shape stopcock 26 is mounted. A liquid such as physiological saline is injected into the introducer sheath 20 from a port of this T-shape stopcock 26 through the tube 25.

For the constituent material of the sheath hub 22, there is no limitation in particular, but a hard material such as a hard resin is preferably used. As specific examples of the hard resin, it is possible to cite, for example, polyolefins such as polyethylene, polypropylene and the like, polyamides, polycarbonates, polystyrenes, and the like.

The hemostasis valve 23 is constituted by an elastic member possessing approximately an elliptical membrane shape (disc shape) and is fixed in a liquid-tight manner with respect to the sheath hub 22.

The constituent material forming the hemostasis valve 23 is not particularly limited. Examples of suitable materials include silicone rubber, latex rubber, butyl rubber, isoprene rubber or the like, which is an elastic member.

The dilator 30 is used, when inserting the introducer sheath 20 into the blood vessel, to prevent breakage of the sheath tube 21, to expand the diameter of a trephination in the skin, and so on.

The dilator tube 31 is inserted inside the sheath tube 21. As shown in FIG. 1, this creates a state in which the distal end 33 of the dilator tube 31 projects distally beyond the distal end of the sheath tube 21.

The constituent material forming the dilator tube 31 is not particularly limited. Examples of materials include a polymer material such as polyolefin (e.g. polyethylene, polypropylene, polybutene, ethylene-propylene copolymer, ethylene-vinyl acetate copolymer, ionomer, a mixture of two kinds or more of these, or the like), polyolefin elastomer, a cross-linked body of polyolefin, polyvinyl chloride, polyamide, polyamide elastomer, polyester, polyester elastomer, polyurethane, polyurethane elastomer, fluororesin, polycarbonate, polystyrene, polyacetal, polyimide, polyetherimide or the like, a mixture of these, or the like.

The dilator hub 32 is held detachably with respect to the sheath hub 22. The constituent material forming the dilator hub 32 is also not limited, but a hard material such as a hard resin is favorably used. As specific examples of the hard resin, it is possible to cite, for example, polyolefins such as polyethylene, polypropylene and the like, polyamides, polycarbonates, polystyrenes, and the like.

Figure 3:
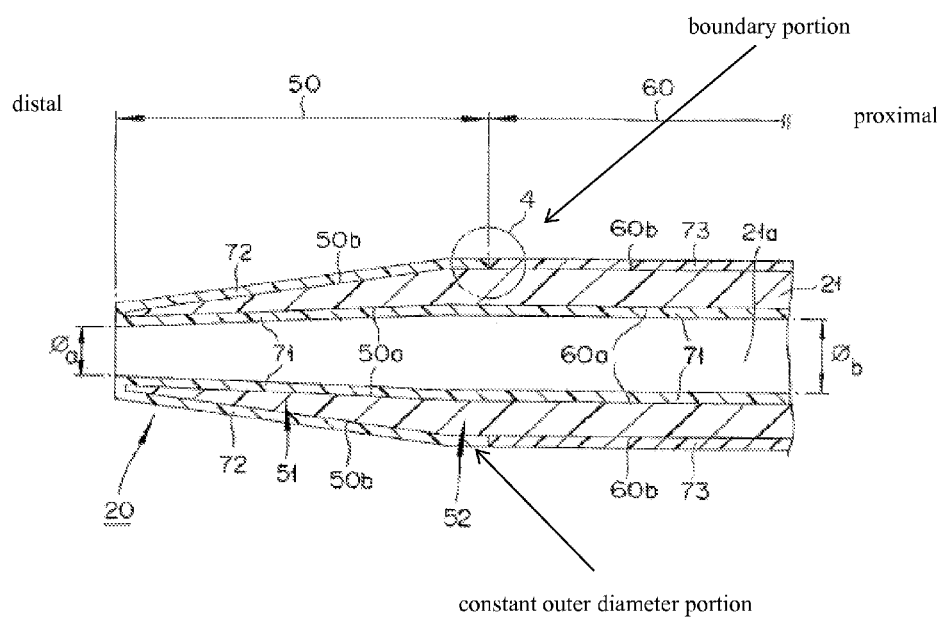
FIG. 3 is a longitudinal cross-sectional view of the introducer sheath disclosed here according to one embodiment disclosed by way of example.
Figure 4A:
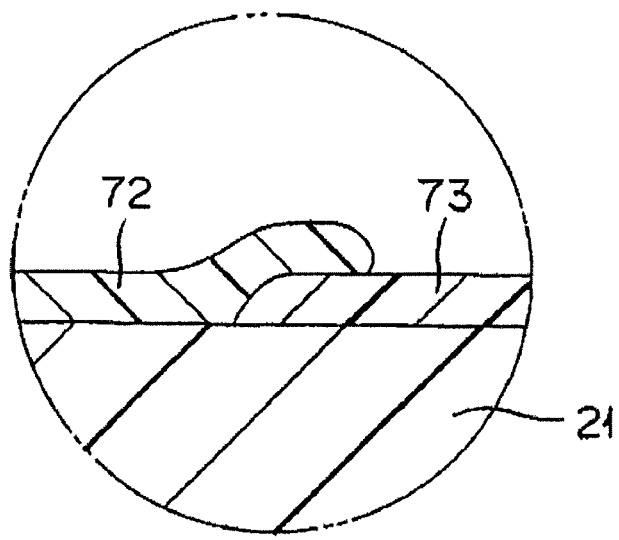
FIG. 4A is an enlarged cross-sectional view of a portion of the introducer sheath which is circled in FIG. 3.

FIGS. 3 and 4A illustrate features and aspects of an introducer sheath 20 according to one example of a first embodiment.

Referring generally to FIG. 3, the introducer sheath 20 is formed by the sheath tube 21 (constituting an example of a tubular member) provided with a hollow portion or through hole 21a through which an elongated body such as a catheter is freely insertable, and the sheath is provided with a sheath distal portion 50 and a sheath main body portion 60. The sheath tube 21 possesses a distal end portion terminating at the distal-most end of the sheath tube 21, and the sheath main body portion 60 has a distal-most end connected to the proximal-most end of the sheath distal portion 50. The sheath distal portion 50 includes a taper portion 51, whose outer diameter tapers in the distal direction from a larger outer diameter to a smaller outer diameter, and a straight portion non-taper portion 52 which extends approximately in parallel with the axis line and which is not tapered.

As for the introducer sheath 20, the inner diameter $\phi_a$ of the sheath distal portion 50 is configured to become gradually smaller toward the distal end of the sheath distal portion 50. The inner diameter of the straight non-taper portion 52 is constant and does not taper. The introducer sheath 20 is further provided, on the inner surface 50a of the sheath distal portion 50, with a hydrophobic coating 71 having a friction coefficient lower than the friction coefficient of the sheath tube 21. In the illustrated example, the hydrophobic coating 71 extends over or covers the entire length of the inner surface 50a of the sheath distal portion 50 and the entire length of the inner surface 60a of the sheath main body portion 60.

The outer surface 50b of the sheath distal portion 50 is further provided with a hydrophobic coating 72. The hydrophobic coating 72 will be described in more detail later.

The introducer sheath 20 is provided with a hydrophilic lubricating coating 73 on the outer surface 60b of the sheath main body portion 60. The introducer sheath 20 is further provided, on the outer surface 50b of the sheath distal portion 50, with the hydrophobic coating 72 having a friction coefficient lower than the friction coefficient of the hydrophilic lubricating coating 73 during the dry period.

Here, the term "dry" such as used in the phrase "during the dry period" broadly means a state in which the hydrophilic lubricating coating 73 is not wet and cannot exert sufficient lubricity. Therefore, it is not necessary to specify the degree of "dry" according to the temperature and the humidity.

Regarding the size of the introducer sheath 20, in a case in which the size of the catheter is 6Fr, the length of the sheath distal portion 50 is 3 mm to 4 mm, the inner diameter $\phi_a$ of the most distal end is 1.98 mm to 2.13 mm and the inner diameter $\phi_b$ of the sheath main body portion 60 is 2.22 mm. The size of the introducer sheath 20 is not limited to the abovementioned dimensions.

The hydrophobic coatings 71, 72 are formed by coating the noted surfaces with a hydrophobic material. Examples of the hydrophobic material include reactive-curing silicone, polytetrafluoroethylene (PTFE), fluorinatedethylenepropylene (FEP) or the like.

The hydrophilic lubricating coating 73 is formed by coating the noted surface with a hydrophilic material. Examples of the hydrophilic material include an acrylamide-based polymer material (e.g., polyacrylamide, a block copolymer of polyglycidylmethacrylate-dimethylacrylamide (PGMA-DMAA)), a cellulose-based polymer material, a polyethylene oxide-based polymer material, a maleic anhydride-based polymer material (e.g., a maleic anhydride copolymer such as methylvinylether-maleic anhydride copolymer), water-soluble nylon, polyvinyl alcohol, polyvinylpyrrolidone or the like.

It is necessary for the hydrophobic coating 72 on the outer surface 50b at the sheath distal portion 50 to at least cover the taper portion 51 of the sheath distal portion 50. The taper portion 51 of the sheath distal portion 50 is a region to which the greatest resistance is applied at the time of insertion. Consequently, when the taper portion 51 which is not provided with the hydrophobic coating 72 is exposed to the outer surface 50b, there occurs a phenomenon that reduction in insertion resistance is hampered and this is the reason for the coating 72. It is desirable for the region provided with the hydrophobic coating 72 within the straight portion 52 of the sheath distal portion 50 to have a range of less than ½ of the effective length of the introducer sheath 20. This is derived in consideration of a balance between the resistance reduction effect at the time when the introducer sheath 20 is inserted and the resistance reduction effect at the time when it is pulled out.

In a case in which the hydrophobic coatings 71, 72 of the inner surface 50a and the outer surface 50b of the sheath distal portion 50 are formed by reactive-curing silicone, the hydrophobic coatings 71, 72 themselves cure and the sheath distal portion 50 cures, thereby making it possible to suppress turn-up of the sheath distal portion 50.

The introducer sheath 20 can be manufactured as follows.

First, the hydrophilic lubricating coating 73 is formed only on the outer surface 60b of the sheath main body portion 60 of the introducer sheath 20. To achieve this, a cored bar is inserted through the sheath tube 21. With the cored bar inside the sheath tube 21, a coating of hydrophilic material is applied to the sheath main body portion 60 of the sheath tube 21 to thereby form the hydrophilic lubricating coating 73. This coating can be applied by, for example, dipping the sheath main body portion 60 of the sheath tube 21 in hydrophilic material. Examples of the hydrophilic material which can be used include polyglycidylmethacrylate-dimethylacrylamide (PGMA-DMAA). Examples of the material which can be used to form the sheath tube 21 include ethylenetetrafluoroethylene copolymer (ETFE).

Subsequently, a process of shape-application on the sheath distal portion 50 is carried out. For this process, there is used a die assembly in which there is formed a recess having an inner-surface shape which conforms to the taper shape of the sheath distal portion 50. The die assembly is heated by a high frequency power supply. The distal end of the sheath tube 21 is pressed into the recess of the die assembly. Then, the inner-surface shape of the recess is transferred to the distal end of the sheath tube 21 and at the sheath distal portion 50, there is formed the taper portion 51 at which the outer surface 50b tapers.

Subsequently, the hydrophobic coating 71 is formed over the whole length of the inner surface 50a of the sheath distal portion 50 and the whole length of the inner surface 60a of the sheath main body portion 60. The inner surfaces 50a, 60a of the introducer sheath 20 are thus coated with a hydrophobic material and the hydrophobic coating 71 is formed. Further, the hydrophobic coating 72 is also formed on the outer surface 50b of the sheath distal portion 50. The sheath distal portion 50 is dipped into a hydrophobic material and the hydrophobic coating 72 is formed. An example of the hydrophobic material which can be used includes reactive-curing silicone is used. As this hydrophobic material, a material is used which has a friction coefficient lower than the friction coefficient of the hydrophilic lubricating coating 73 during the dry period thereof. In the above-mentioned example, reactive-curing silicone having a friction coefficient lower than the friction coefficient of ETFE during the dry period thereof is used as the hydrophobic material.

By way of the processes mentioned above, the introducer sheath 20 shown in FIG. 3 is formed.

For the introducer sheath 20 of this disclosed example of the first embodiment, the inner diameter $\phi_a$ of the most distal end of the sheath 20 is smaller than the outer diameter of the elongated body such as a catheter which is to be inserted into the sheath 20, but on the inner surface 50a of the sheath distal portion 50, there is provided the hydrophobic coating 71 (coating composed of reactive-curing silicone) having a friction coefficient lower than the friction coefficient of the raw material (e.g., ETFE) of the sheath tube 21. Consequently, the sliding resistance between the inner surface 50a of the sheath distal portion 50 and the elongated body such as a catheter is lowered, and it is possible to achieve improvement in the slidability of the catheter or the like.

If the inner surface 50a of the sheath distal portion 50 was provided with a hydrophilic lubricating coating, a process for activating the raw material of the sheath tube 21 would be necessary, and it would be necessary to form the hydrophilic lubricating coating before carrying out the shape-application process on the sheath distal portion 50. The heat created at the time of carrying out the shape-application process on the sheath distal portion 50 using the die assembly acts excessively and there occurs a phenomenon that the hydrophilic coating peels, decomposes, degrades or the like. Consequently, the sliding resistance between the inner surface 50a of the sheath distal portion 50 and the elongated body such as a catheter would not be lowered substantially, and so it would not be possible to achieve improvement in the slidability of the elongated body such as the catheter or the like.

On the other hand, in the case of the hydrophobic coating 71 on the inner surface 50a of the sheath distal portion 50, the coating 71 can be formed by coating with a hydrophobic material after carrying out the shape-application process on the sheath distal portion 50. Peeling, decomposition, degradation and the like of the hydrophobic coating 71 thus do not occur. Therefore, as mentioned above, the sliding resistance between the inner surface 50a of the sheath distal portion 50 and the elongated body such as a catheter is lowered and it is possible to achieve improvement in the slidability of the elongated body such as the catheter or the like.

The introducer sheath 20 is further provided with the hydrophobic coating 72 having a friction coefficient lower than the friction coefficient of the hydrophilic lubricating coating 73 during the dry period of the coating 73, on the outer surface 50b of the sheath distal portion 50 to which the greatest resistance is applied at the time of insertion. The hydrophilic coating has a poor sliding property under a dry condition, but by providing the hydrophobic coating 72 on the outer surface 50b of the sheath distal portion 50, it is possible to lower the insertion resistance of the introducer sheath 20 when inserting the sheath from the skin into the blood vessel. When pulling out the introducer sheath 20 after its insertion into the blood vessel, the hydrophilic lubricating coating 73 becomes wet by the blood and exhibits lubricity, so that it is possible to pull it out relatively smoothly. Preferably, the hydrophilic lubricating coating 73 and the hydrophobic coating 72 are configured so that when the hydrophilic lubricating coating swells by absorbing blood, the hydrophilic lubricating coating has an outer diameter approximately equal to or greater than the outer diameter of the hydrophobic coating.

In this manner, according to the introducer sheath 20 of the first embodiment disclosed by way of example, even in a case in which the inner diameter φa of the sheath distal portion 50 is configured to become gradually smaller toward the distal end, it is possible to achieve improvement in the slidability of the elongated body such as a catheter. Furthermore, according to the introducer sheath 20 of this embodiment, it is possible to achieve reduction in the insertion resistance even under a dry condition at the beginning of the use thereof.

FIG. 4A shows a structure in which the hydrophobic coating 72 on the outer surface 50b of the sheath distal portion 50 and the hydrophilic lubricating coating 73 on the outer surface 60b of the sheath main body portion 60 axially overlap each other.

As shown in FIG. 4A, at the boundary portion between the sheath distal portion 50 and the sheath main body portion 60, it is desirable to employ a structure in which the hydrophobic coating 72 overlies the hydrophilic lubricating coating 73. This is because at the time of insertion of the introducer sheath 20 from the skin (through the skin) into the blood vessel, the sheath does not get stuck on the end surface of the hydrophilic lubricating coating 73 at the boundary portion. By employing such a construction, it is possible to relatively smoothly insert the introducer sheath 20 and it is even possible to suppress peeling of the hydrophilic lubricating coating 73.

Figure 4B:
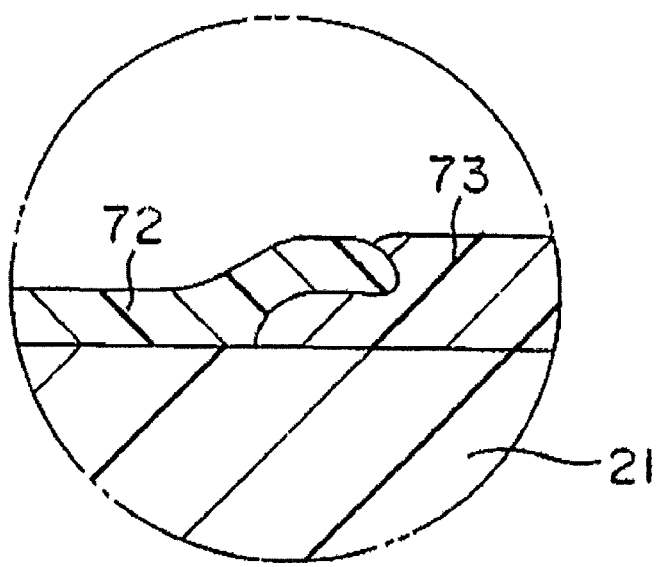
FIG. 4B is a cross-sectional view similar to FIG. 4A showing a state after an introducer sheath is inserted inside a lumen in a living body (e.g., a blood vessel).

FIG. 4B shows the state of the hydrophilic lubricating coating 73 and the hydrophobic coating 72 after insertion of the introducer sheath 20 into the blood vessel.

As shown in FIG. 4B, the hydrophilic lubricating coating 73 absorbs blood and swells, and the diameter of the hydrophilic lubricating coating 73 becomes approximately equal to or larger than the outer diameter of the hydrophobic coating 72. By virtue of this, when the introducer sheath 20 is pulled out from the blood vessel, the overlapping portion at which the proximal portion of the hydrophobic coating 72 axially overlaps the distal portion of the hydrophilic lubricating coating 73 does not exhibit a significant level difference. That is, the larger outer diameter of the proximal portion of the hydrophobic coating 72 relative to the outer diameter of the distal portion of the hydrophilic lubricating coating 73 that exists before insertion of the introducer sheath 20 into the blood vessel as shown in FIG. 4A is preferably eliminated, so that after insertion of the introducer sheath 20 into a blood vessel as shown in FIG. 4B, the outer diameter of the distal portion of the hydrophilic lubricating coating 73 is equal to or larger than the outer diameter of the proximal portion of the hydrophobic coating 72. Therefore, the resistance of the surface of the introducer sheath 20 with respect to the blood vessel and the puncture site of the skin does not become excessive and it is possible to pull out the introducer sheath 20 relatively smoothly due to both the coatings 72 and 73.

According to experimentation, by providing the hydrophobic coating 71 formed from reactive-curing silicone, the sliding resistance of the inner surface 50a at the sheath distal portion 50 is lowered by as much as approximately 80% compared with a case in which the hydrophobic coating 71 was not applied. Further, by providing the hydrophobic coating 72 formed from reactive-curing silicone, the penetration resistance of the outer surface 50b at the sheath distal portion 50 is lowered by as much as approximately 30% compared with a case in which a hydrophilic lubricating coating was applied. In this manner, it was confirmed by experimentation that high effectiveness can be obtained both in relation to reduction in the sliding resistance of the inner surface 50a at the sheath distal portion 50 and in relation to reduction in the penetration resistance of the outer surface 50b at the sheath distal portion 50.

Figure 5:
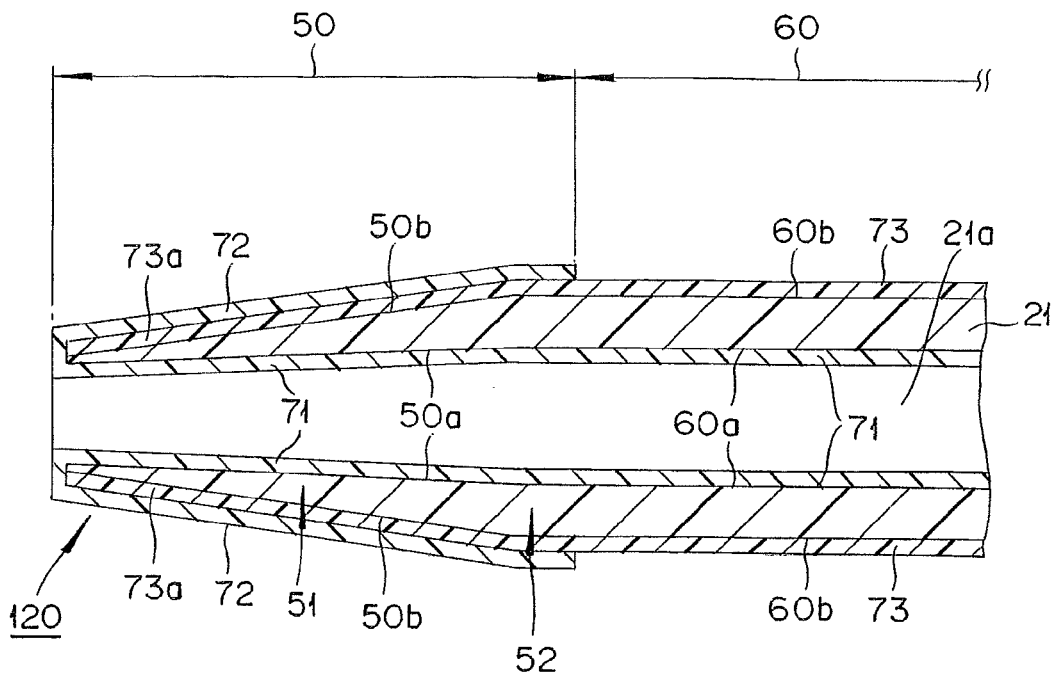
FIG. 5 is a longitudinal cross-sectional view of an introducer sheath according to a second embodiment.

FIG. 5 illustrates an introducer sheath according to a second embodiment which represents a modified example of the first embodiment.

This second embodiment is an example in which the manufacturing procedure of an introducer sheath 120 is modified with respect to the first embodiment described above.

In the manufacturing procedure associated with manufacturing the embodiment shown in FIG. 5, first, the hydrophilic lubricating coating 73 is formed not only on the outer surface 60b of the sheath main body portion 60 of the introducer sheath 120 but also on the outer surface 50b of the sheath distal portion 50. A cored bar is inserted through the sheath tube 21, and by dipping the sheath tube with cored bar into a hydrophilic material, the hydrophilic lubricating coating 73 is formed on the whole or entirety of the outer surfaces 50b, 60b of the introducer sheath 120.

Subsequently, a shape-application process on the sheath distal portion 50 is carried out. Depending on the heat which acts or is created when the shape-application process on the sheath distal portion 50 is carried out using a die assembly, the hydrophilic lubricating coating 73 on the outer surface 50b of the sheath distal portion 50 disappears, the lubricity thereof is deactivated although the coating itself remains, and the like. This second embodiment shows the latter state in which the lubricity is deactivated, though the coating itself remains. As shown in FIG. 5, the coating 73a whose lubricity has been deactivated remains on the outer circumference surface 50b of the sheath distal portion 50.

Subsequently, the hydrophobic coating 71 is formed over the entire length of the inner surface 50a of the sheath distal portion 50 and over the entire length of the inner surface 60a of the sheath main body portion 60. The inner surfaces 50a, 60a of the introducer sheath 20 are thus coated with a hydrophobic material and the hydrophobic coating 71 is formed. Further, the hydrophobic coating 72 is formed also on the outer surface of the coating 73a, whose lubricity has been deactivated, at the sheath distal portion 50. By dipping the sheath distal portion 50 into a hydrophobic material, the hydrophobic coating 72 is formed.

By way of the processes mentioned above, the introducer sheath 120 shown in FIG. 5 is formed. In this embodiment of the introducer sheath disclosed by way of example, the hydrophobic coating 72 is formed on the coating 73a whose lubricity has been deactivated, so that functional groups remaining in the coating 73a are coupled with the hydrophobic coating. Consequently, it is possible to improve the fixation property compared with a case in which a sheath made of ethylene-tetra-fluoro-ethylene copolymer (ETFE) is directly covered with a hydrophobic coating.

Figure 6:
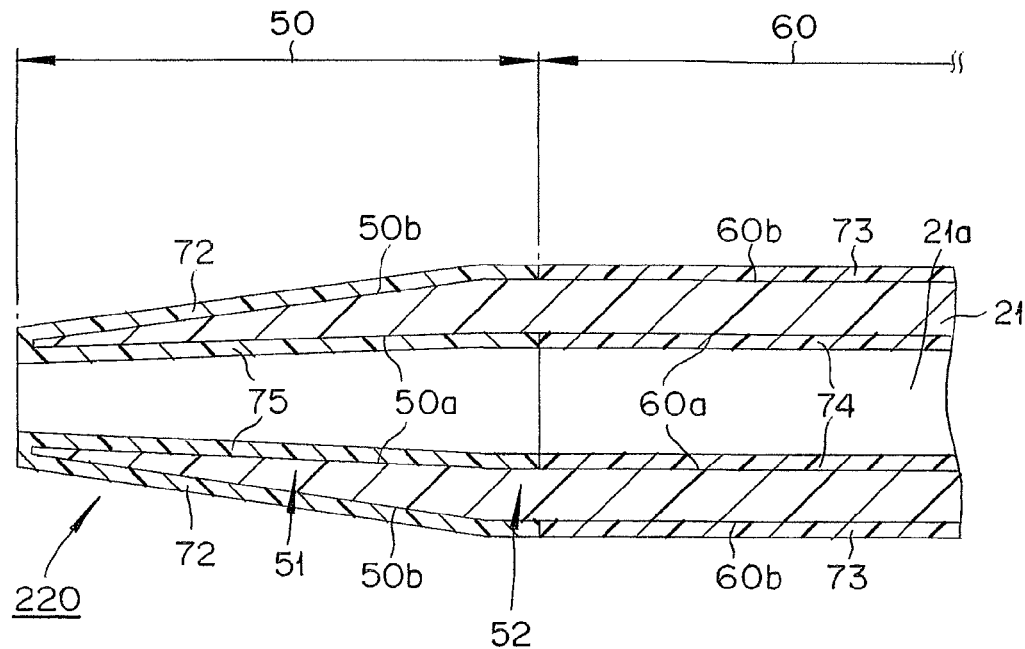
FIG. 6 is a longitudinal cross-sectional view of an introducer sheath according to a third embodiment.

FIG. 6 illustrates an introducer sheath 220 according to a third embodiment.

With reference to FIG. 6, the introducer sheath 220 of this embodiment includes a hydrophilic lubricating coating 74 on the inner surface 60a of the sheath main body portion 60 and in terms of this aspect, it is different from the introducer sheath 20 of the first embodiment which is provided with the hydrophobic coating 71 on the inner surface 60a of the sheath main body portion 60.

The introducer sheath 220 of this embodiment, similar to the first embodiment described above by way of example, possesses an inner diameter $\phi_a$ of the sheath distal portion 50 that becomes gradually smaller toward the distal side. The inner surface 50a of the sheath distal portion 50 is provided with a hydrophobic coating 75 having a friction coefficient lower than the friction coefficient of the sheath tube 21. Also, for the introducer sheath 220, similar to the first embodiment, the hydrophilic lubricating coating 73 is provided on the outer surface 60b of the sheath main body portion 60, and the hydrophobic coating 72 having a friction coefficient lower than the friction coefficient of the hydrophilic lubricating coating 73 during the dry period thereof is provided on the outer surface 50b of the sheath distal portion 50.

The size, the hydrophobic material and the hydrophilic material of the introducer sheath 220 are similar to those of the first embodiment described above.

The introducer sheath 220 is manufactured as follows.

First, the inner surfaces 50a, 60a and the outer surfaces 50b, 60b of the introducer sheath 220 are subjected to plasma treatment so that a process for activating the raw-material surface layer of the sheath tube 21 is carried out.

Subsequently, the hydrophilic lubricating coatings 73, 74 are formed on the inner surfaces 50a, 60a and the outer surfaces 50b, 60b of the introducer sheath 220. By dipping the inner surfaces 50a, 60a and the outer surfaces 50b, 60b of the sheath tube 21 into a hydrophilic material, the hydrophilic lubricating coating 73 is formed. The hydrophilic material used is, for example, polyglycidylmethacrylate-dimethylacrylamide (PGMA-DMAA) or the like. The material of the sheath tube 21 is, for example, ethylenetetrafluoroethylene copolymer (ETFE) or the like.

Subsequently, a shape-application process on the sheath distal portion 50 is carried out. In this process, a die assembly is used in which there is formed a recess having an inner-surface shape which conforms to the tapered outer shape of the sheath distal portion 50. The die assembly is heated by a high frequency power supply. The distal end of the sheath tube 21 is pressed into the recess of the die assembly. Then, the inner-surface shape of the recess is transferred to the distal end of the sheath tube 21, and the sheath distal portion 50 is formed with the taper portion 51 at which the outer surface 50b tapers. In the former process, at the time of dipping into the hydrophilic material, the hydrophilic lubricating coating is formed on the inner surface 50a and the outer surface 50b of the sheath distal portion 50. However, depending on the heat which acts at the time of carrying out the shape-application process on the sheath distal portion 50 by using the die assembly, the hydrophilic lubricating coating on the inner surface 50a and the outer surface 50b of the sheath distal portion 50 disappears, the lubricity thereof is deactivated, though the coating itself remains, and so on. This second modified embodiment shows the former state in which the hydrophilic lubricating coating has disappeared due to the shape-application process.

Subsequently, the hydrophobic coatings 75, 72 are formed on the inner surface 50a and the outer surface 50b of the sheath distal portion 50. The hydrophobic coatings 75, 72 are formed at the portions at which the hydrophilic lubricating coating has disappeared. By dipping the sheath distal portion 50 into a hydrophobic material, the hydrophobic coatings 75, 72 are formed. Examples of the hydrophobic material used include reactive-curing silicone or the like. For this hydrophobic material, a material is used which has a friction coefficient lower than the friction coefficient of the hydrophilic lubricating coating 73 during the dry period thereof. In the above-mentioned example, reactive-curing silicone having a friction coefficient lower than the friction coefficient of ETFE during the dry period thereof is used as the hydrophobic material.

By way of the processes mentioned above, the introducer sheath 220 shown in FIG. 6 is formed.

For the introducer sheath 220 of this third embodiment, similar to the embodiments described above, the inner diameter φa of the most distal end of the sheath is smaller than the outer diameter of the elongated body such as a catheter, but on the inner surface 50a of the sheath distal portion 50, there is provided the hydrophobic coating 75 (coating composed of reactive-curing silicone) having a friction coefficient lower than the friction coefficient of the raw material (e.g., ETFE) of the sheath tube 21. Consequently, the sliding resistance between the inner surface 50a of the sheath distal portion 50 and the elongated body such as a catheter is lowered, which makes it possible to achieve improvement in the slidability of the catheter or the like.

Also, in case of forming the hydrophobic coatings 75, 72 on the inner surface 50a and the outer surface 50b of the sheath distal portion 50, it is possible to form them by dipping into a hydrophobic material after carrying out the shape-application process on the sheath distal portion 50, and peeling, decomposition, degradation and the like of the hydrophobic coatings 75, 72 do not occur. Therefore, as mentioned above, the sliding resistance between the inner surface 50a of the sheath distal portion 50 and the elongated body such as a catheter is lowered, in which it is possible to achieve improvement in the slidability of the catheter or the like. The introducer sheath 220 is further provided with the hydrophobic coating 72 having a friction coefficient lower than the friction coefficient of the hydrophilic lubricating coating 73 during the dry period thereof, on the outer surface 50b of the sheath distal portion 50. The hydrophilic coating has a poor sliding property under a dry condition, but by providing the hydrophobic coating 72 on the outer surface 50b of the sheath distal portion 50, it is possible to lower the insertion resistance of the introducer sheath 220 when inserting it from (through) the skin into the blood vessel. When the introducer sheath 220 is pulled out after its insertion it into the blood vessel, the hydrophilic coating becomes wet by the blood and exhibits lubricity, so that it is possible to pull it out rather smoothly.

In this manner, according to the introducer sheath 220 of the third embodiment disclosed by way of example, even in a case in which the inner diameter $\phi_a$ of the sheath distal portion 50 gradually becomes smaller toward the distal end, it is possible to achieve improvement in the slidability of the elongated body such as a catheter and furthermore, it is possible to achieve reduction in insertion resistance even under a dry condition at the beginning of use.

Similar to the first embodiment described above, it is desirable for the boundary portion between the sheath distal portion 50 and the sheath main body portion 60 to employ a structure in which the hydrophobic coating 72 lies over the hydrophilic lubricating coating 73 as shown in FIG. 4A. This is because it is possible to insert the introducer sheath 220 relatively smoothly and it is also possible to suppress peeling of the hydrophilic lubricating coating 73.

Figure 7:
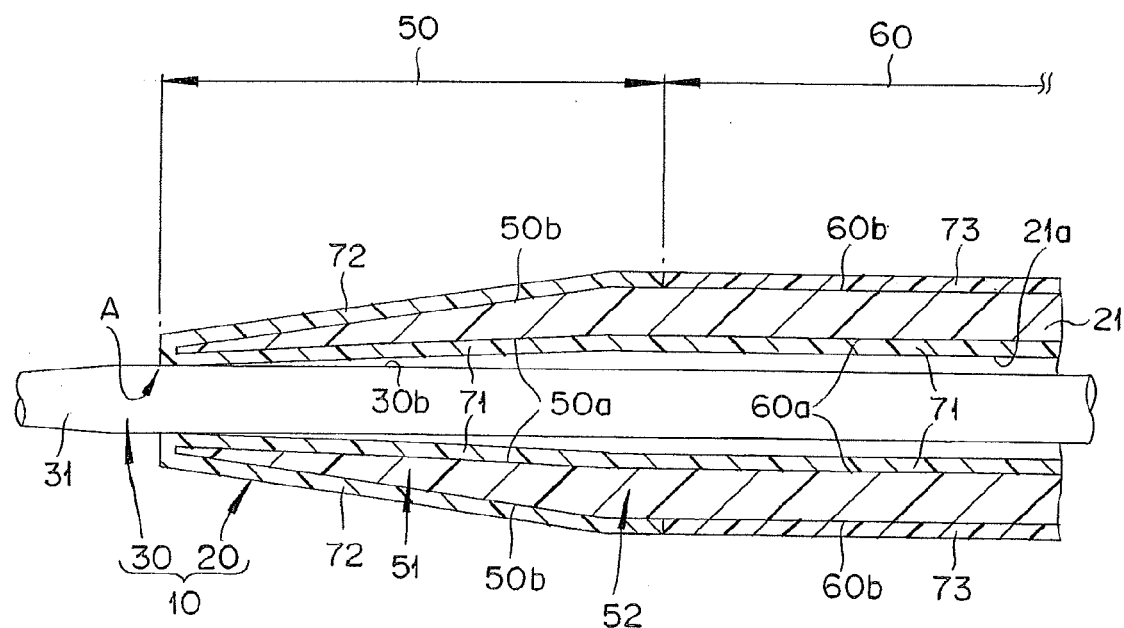
FIG. 7 is a longitudinal cross-sectional view of an introducer sheath according to a fourth embodiment.

FIG. 7 illustrates the introducer sheath 20 and the dilator 30 in an introducer assembly 10 according to another embodiment.

The introducer assembly 10 is constituted such that the dilator 30 as an elongated body is inserted through the introducer sheath 20 of the first embodiment and the distal end of the dilator tube 31 of the dilator 30 projects from (i.e., distally beyond) the sheath distal portion 50. In this introducer assembly 10, at least a portion of the inner surface 50a of the sheath distal portion 50 and a portion of the outer surface 30b of the dilator 30 are attached to each other through the hydrophobic coating 71. In the drawing, the sheath distal portion 50 and the dilator 30 are attached to each other at the portion indicated by a reference numeral A.

By attaching the sheath distal portion 50 and the dilator 30 to each other, a turn-up of the sheath distal portion 50 is suppressed when the introducer sheath 20 is inserted from (through) the skin into the blood vessel, whereby it is possible to insert the introducer sheath 20 rather smoothly.

There is no specific limitation on the region (axial extent of the region) at which the inner surface 50a of the sheath distal portion 50 and the outer surface 30b of the dilator 30 are attached to each other, but from a view point of suppressing turn-up of the sheath distal portion 50, it is preferable to perform the attachment at the position which nears the distal end side as much as possible.

It is possible for the hydrophobic coating 71 to be formed by a reactive-curing coating material, for example reactive-curing silicone. In this case, it is desirable for the hydrophobic coating 71 to be formed by reactively curing the coating material in a state in which the dilator 30 is inserted through the introducer sheath 20. This is because, according to such an introducer assembly 10, it is possible to simultaneously carry out formation of the hydrophobic coating 71 and attachment between the inner surface 50a of the sheath distal portion 50 and the outer surface 30b of the dilator 30 through this hydrophobic coating 71 and it is possible to achieve simplification of the manufacturing process.

Further, by forming the hydrophobic coatings 71, 72 on the inner surface 50a and the outer surface 50b of the sheath distal portion 50 from the curing reactive silicone, the hydrophobic coatings 71, 72 themselves cure, and the sheath distal portion 50 cures, which makes it possible to suppress turn-up of the sheath distal portion 50 even further.

In the introducer assembly 10, it is desirable for the force, by which the introducer sheath 20 and the dilator 30 are attached to each other, to be smaller than the force which acts on the attachment region when the dilator 30 is pulled out from the introducer sheath 20.

This is because, by configuring the attachment region to be a breakable attachment region at which the attachment between the inner surface 50a of the sheath distal portion 50 and the outer surface 30b of the dilator 30 is breakable, it is possible to use or operate the introducer assembly 10 while maintaining similar feelings felt until without the attachment, which does not give uncomfortable feelings to the operator.

The introducer assembly 10 makes it possible to attach the introducer sheath 20 and the dilator 30 to each other by reactively curing a coating material depending on the heat at the time of gas sterilization.

This is because, according to such an introducer assembly 10, it is possible to simultaneously carry out formation of the hydrophobic coating 71 and attachment of the introducer sheath 20 and the dilator 30 to each other through this hydrophobic coating 71 in a packed state at the time of EOG sterilization, whereby it is possible to achieve simplification of the manufacturing process.

Figure 8:
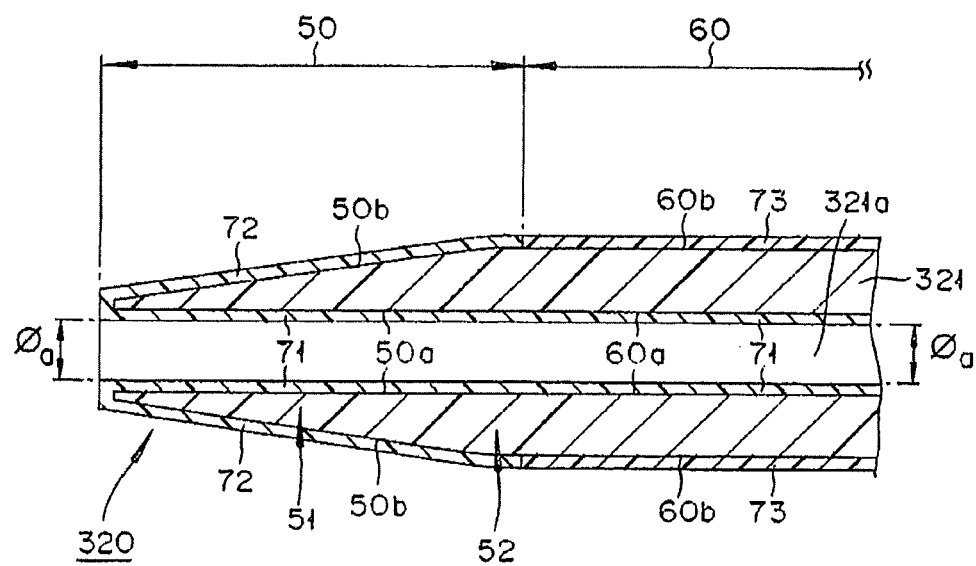
FIG. 8 is a longitudinal cross-sectional view of an introducer sheath according to a further embodiment.

FIG. 8 is a cross-sectional view showing an introducer sheath 320 according to a further embodiment.

With respect to the introducer sheaths 20, 120, 220 mentioned above, the inner diameter $\phi_a$ of the sheath distal portion 50 is formed to become gradually smaller toward the distal side and on the inner surface 50a of the sheath distal portion 50, and there is formed the hydrophobic coating 71 having a friction coefficient lower than the friction coefficient of the sheath tube 21. It is possible to lower the sliding resistance of the inner surface 50a by providing the hydrophobic coating 71, so that it becomes possible to achieve reduction in sliding resistance even if the contact area with respect to the catheter or the like increases.

The introducer sheath 320 of this embodiment shown in FIG. 8 employs a configuration in which the inner diameter of the sheath distal portion 50 is formed with uniform size without diameter reduction. In terms of this aspect, this fourth modified version of the introducer sheath differs from the first to third embodiments.

In more detail, as shown in FIG. 8, the introducer sheath 320 according to this embodiment is formed by a sheath tube 321 (corresponding to tubular member) provided with a hollow portion 321a through which the elongated body such as a catheter is freely insertable. The introducer sheath 320 is provided with the sheath distal portion 50 (corresponding to distal portion) and the sheath main body 60 (corresponding to main body portion). The sheath distal portion 50 includes a taper portion 51 which tapers and a straight portion 52 which extends approximately in parallel with the axial line.

As for the introducer sheath 320, the inner diameter of the sheath distal portion 50 is not reduced and is formed uniformly as the inner diameter $\phi_a$. Also the inner diameter of the sheath main body 60 is formed uniformly as the inner diameter $\phi_a$. The introducer sheath 320 is further provided, on the inner surface 50a of the sheath distal portion 50, with the hydrophobic coating 71 having a friction coefficient lower than the friction coefficient of the sheath tube 321. In this fourth exemplified embodiment, there is provided the hydrophobic coating 71 over the whole lengths of the inner surface 50*a* of the sheath distal portion 50 and the inner surface 60*a* of the sheath main body 60.

With respect to an aspect in which there is provided, on the outer surface 60*b* sheath main body 60, the hydrophilic lubricating coating 73; an aspect in which there is provided, on the outer surface 50*b* of the sheath distal portion 50, the hydrophobic coating 72 having a friction coefficient lower than the friction coefficient of the hydrophilic lubricating coating 73 during the dry period thereof; an aspect of the constituent materials of the sheath tube 321; an aspect of the constituent materials of the hydrophobic coatings 71, 72; and an aspect of the constituent materials of the lubricating coating 73, they are similar to those explained in the first exemplified embodiment. As for the manufacturing procedure of the introducer sheath 320, it is similar to that explained in the first exemplified embodiment except an aspect in which a straight-shape cored bar is inserted through the sheath tube 321 such that the inner diameter of the sheath tube 321 is not reduced when carrying out the shape-application process on the sheath distal portion 50.

According to the introducer sheath 320 of this embodiment, it is possible to achieve improvement in the slidability of the elongated body such as a catheter even in case of forming the inner diameter of the sheath tube 321 uniformly. Furthermore, according to the introducer sheath 320, it is possible to achieve reduction in insertion resistance even under a dry condition at the beginning of the use thereof.

The introducer sheaths 20, 120, 220, 320 and the introducer assembly 10 disclosed here were explained based on various embodiments disclosed and illustrated in the drawing figures by way of example. But it is possible to employ features and aspects varying from those described and illustrated.

For example, in a case in which reduction in the sliding resistance of the inner surface 50*a* in the sheath distal portion 50 is to be mainly achieved, it is sufficient if the inner diameter $\phi_a$ of the sheath distal portion 50 is configured so that it becomes gradually smaller toward the distal side and only the hydrophobic coating 71 having a friction coefficient lower than the friction coefficient of the sheath tube 21 is formed only on the inner surface 50*a* of the sheath distal portion 50.

Also, in a case in which reduction in the penetration resistance of the outer surface 50*b* in the sheath distal portion 50 is to be mainly achieved, it is sufficient if the hydrophilic lubricating coating 73 is provided on the outer surface 60*b* of the sheath main body portion 60 and the hydrophobic coating 72 having a friction coefficient lower than the friction coefficient of the hydrophilic lubricating coating 73 during the dry period thereof is formed on the outer surface 50*b* of the sheath distal portion 50. In this case, the hydrophobic coating of the inner surface 50*a* in the sheath distal portion 50 is not indispensable.

The detailed description above describes features and aspects of embodiments of an introducer sheath and introduce assembly. But the invention here is not limited to the precise embodiments and variations described. Changes, modifications and equivalents can be employed by one skilled in the art without departing from the spirit and scope of the invention as defined in the appended claims. It is expressly intended that all such changes, modifications and equivalents which fall within the scope of the claims are embraced by the claims.

What is claimed is:

1. An introducer sheath comprising:
an elongated tubular member possessing a distal-most end and configured to be inserted in a living body tissue, the distal-most end of the elongated tubular member having an opening, the tubular member including a distal portion and a main body portion portion;

the distal portion terminating distally at the distal-most end of the tubular member, the distal portion possessing an outer surface;

the main body portion having a distal-most end connected to and extending proximally from a proximal-most end of the distal portion so that the main body portion is located entirely proximally of the distal portion, the main body portion possessing an outer surface;

the elongated tubular member including a through hole extending throughout a longitudinal extent of the tubular member and opening to the distal-most end of the elongated tubular member, the through hole being configured to receive an elongated body, the through hole possessing an inner diameter;

the distal portion of the elongated tubular member being comprised of a taper portion in which the inner diameter of the through hole gradually and continuously tapers to the distal-most end of the elongated tubular member so that the inner diameter is smallest at the distal-most end of the tubular member, the taper portion possessing an outer surface;

a hydrophilic lubricating coating on an outer surface of the main body portion;

a hydrophobic coating on the inner surface of the through hole in the taper portion, the hydrophobic coating extending proximally from the distal-most end of the tubular member toward the main body portion;

the hydrophobic coating possessing a friction coefficient lower than a friction coefficient of the hydrophilic lubricating coating before the hydrophilic lubricating coating contacts liquid;

wherein the taper portion possesses an outer diameter that gradually and continuously tapers to the distal-most end of the elongated tubular member so that the outer diameter is smallest at the distal-most end of the tubular member; and a hydrophobic coating covering the entire outer surface of the taper portion of the distal portion of the elongated tubular member.

2. The introducer sheath according to claim 1, wherein the hydrophobic coating on the inner surface of the through hole extends continuously from the distal-most end of the tubular member, throughout the entirety of the longitudinal extent of the taper portion and into the main body portion of the tubular member.

3. The introducer sheath according to claim 2, wherein the inner diameter of the through hole in the main body portion does not taper in a narrowing manner toward the distal portion.

4. The introducer sheath according to claim 3, wherein the hydrophobic coating covering the entire outer surface of the taper portion also covers the outer surface of a part of the distal portion which possesses a constant outer diameter.

5. The introducer sheath according to claim 1, wherein the distal portion of the elongated tubular member includes a non-taper portion positioned entirely proximally of the taper portion, the inner diameter of the through hole in the non-taper portion being constant, and the hydrophobic coating extending continuously from the distal-most end of the tubular member through the taper portion, the non-taper portion, and into the main body portion of the tubular member.

6. The introducer sheath according to claim 1, wherein the distal-most end of the main body portion is connected to the proximal-most end of the distal portion at a boundary portion, the hydrophobic coating overlying the hydrophilic lubricating coating at the boundary portion.

7. The introducer sheath according to claim 1, wherein the distal portion of the elongated tubular member includes a constant outer diameter portion, and the hydrophobic coating which covers the entire outer surface of the taper portion of the distal portion of the elongated tubular member also covers at least a part of the outer surface of the constant outer diameter portion.

8. The introducer sheath according to claim 1, wherein at least a portion of the hydrophobic coating which covers the entire outer surface of the taper portion of the distal portion of the elongated tubular member overlies the hydrophilic lubricating coating.

9. An introducer sheath comprising:
  a tubular member possessing a hollow portion through which an elongated body is freely insertable, the tubular member including a distal portion and a main body portion, the main body portion being positioned proximally of the distal portion;
  the hollow portion of the distal portion possessing an inner diameter which becomes gradually smaller toward a distal end of the tubular member;
  the distal portion possessing an inner surface provided with a hydrophobic coating having a friction coefficient lower than the friction coefficient of the tubular member;
  a hydrophobic coating being disposed on an outer surface of the distal portion;
  the main body portion possessing an outer surface;
  a hydrophilic lubricating coating being disposed on the outer surface of the main body portion; and
  the hydrophobic coating possessing a friction coefficient lower than a friction coefficient of the hydrophilic lubricating coating before the hydrophilic lubricating coating contacts liquid.

10. The introducer sheath according to claim 9, wherein at a boundary portion between the distal portion and the main body portion, the hydrophobic coating overlies the hydrophilic lubricating coating.

11. The introducer sheath according to claim 9, wherein when swelling by absorbing blood, the hydrophilic lubricating coating has an outer diameter approximately equal to or greater than the outer diameter of the hydrophobic coating.

12. The introducer sheath according to claim 9, wherein the hydrophobic coating on the inner surface of the distal portion extends continuously from a distal-most end of the tubular member through the hollow portion of the distal portion and into the main body portion of the tubular member.

13. The introducer sheath according to claim 9, wherein the hollow portion in the main body portion has an inner diameter that does not taper in a narrowing manner toward the distal portion.

14. The introducer sheath according to claim 9, wherein at least a portion of the hydrophobic coating which covers the outer surface of the distal portion of the tubular member also overlies the hydrophilic lubricating coating.

15. An introducer sheath comprising:
  an elongated tubular member possessing a distal-most end and configured to be inserted in a living body tissue, the distal-most end of the elongated tubular member having an opening, the tubular member including a distal portion and a main body portion;
  the distal portion terminating distally at the distal-most end of the tubular member, the distal portion possessing an outer surface;
  the main body portion having a distal-most end connected to and extending proximally from a proximal-most end of the distal portion so that the main body portion is located entirely proximally of the distal portion, the main body portion possessing an outer surface;
  the elongated tubular member including a through hole extending throughout a longitudinal extent of the tubular member and opening to the distal-most end of the elongated tubular member, the through hole being configured to receive an elongated body, the through hole possessing an inner diameter;
  the distal portion of the elongated tubular member being comprised of a taper portion in which the inner diameter of the through hole gradually and continuously tapers to the distal-most end of the elongated tubular member so that the inner diameter of the through hole in the taper portion is smallest at the distal-most end of the tubular member, the taper portion possessing an outer surface;
  a hydrophilic lubricating coating on the outer surface of the main body portion;
  a hydrophobic coating on an inner surface of the through hole in the taper portion, the hydrophobic coating extending proximally from the distal-most end of the tubular member toward the main body portion;
  the hydrophobic coating possessing a friction coefficient lower than a friction coefficient of the hydrophilic lubricating coating before the hydrophilic lubricating coating contacts liquid;
  a hydrophobic coating covering the outer surface of the taper portion of the distal portion of the elongated tubular member; and
  wherein at least a portion of the hydrophobic coating covering the outer surface of the taper portion of the distal portion of the elongated tubular member overlies the hydrophilic lubricating coating.

* * * * *